(12) United States Patent
Zawierucha et al.

(10) Patent No.: US 8,080,497 B2
(45) Date of Patent: Dec. 20, 2011

(54) **METHOD OF CONTROLLING THE AQUATIC WEED *HYDRILLA VERTICILLATA***

(75) Inventors: Joseph Zawierucha, Cary, NC (US); W. Glenn Oliver, Apex, NC (US); Rick Evans, Raleigh, NC (US); Todd Horton, Anderson, SC (US); Daniel D. Beran, Des Moines, IA (US); Joseph G. Vollmer, Laramie, WY (US); Alane J-Bo Burns, Raleigh, NC (US); Jeffrey H. Birk, Raleigh, NC (US); Derek W. Miller, Apex, NC (US); Timothy P. Knight, Raleigh, NC (US)

(73) Assignee: BASF SE, Ludwigshafen (DE)

( * ) Notice: Subject to any disclaimer, the term of this patent is extended or adjusted under 35 U.S.C. 154(b) by 532 days.

(21) Appl. No.: 12/158,230

(22) PCT Filed: Dec. 18, 2006

(86) PCT No.: PCT/EP2006/069861
§ 371 (c)(1),
(2), (4) Date: Jun. 19, 2008

(87) PCT Pub. No.: WO2007/071655
PCT Pub. Date: Jun. 28, 2007

(65) Prior Publication Data
US 2008/0305954 A1    Dec. 11, 2008

Related U.S. Application Data

(60) Provisional application No. 60/752,906, filed on Dec. 23, 2005.

(51) Int. Cl.
*A01N 43/36* (2006.01)
(52) U.S. Cl. ...................... 504/156; 514/235.8
(58) Field of Classification Search .................. 504/156, 504/253; 514/235.8
See application file for complete search history.

(56) References Cited

U.S. PATENT DOCUMENTS

| | | | |
|---|---|---|---|
| 4,398,937 A | 8/1983 | Van Aller et al. | |
| 4,497,651 A | 2/1985 | Hagen et al. | |
| 4,632,696 A | 12/1986 | Hagen et al. | |
| 4,715,889 A | 12/1987 | Hagen et al. | |
| 4,798,619 A | 1/1989 | Los | |
| 5,334,576 A | 8/1994 | Doehner, Jr. et al. | |
| 5,973,154 A | 10/1999 | Drabb et al. | |
| 6,121,203 A * | 9/2000 | Alby, III | 504/253 |
| 6,339,158 B1 | 1/2002 | Wepplo et al. | |
| 6,677,276 B1 | 1/2004 | Hacker et al. | |
| 2002/0119891 A1 | 8/2002 | Netherland | |
| 2003/0186815 A1 | 10/2003 | Hacker et al. | |
| 2009/0011934 A1 | 1/2009 | Zawierucha et al. | |
| 2010/0093540 A1 | 4/2010 | Horton et al. | |

FOREIGN PATENT DOCUMENTS

| | | |
|---|---|---|
| CN | 1401232 | 3/2003 |
| EP | 0 094 181 | 11/1983 |
| EP | 0 127 433 | 12/1984 |
| WO | WO 2005/077169 | 8/2005 |
| WO | WO 2005096814 A2 * | 10/2005 |
| WO | WO 2007/014758 | 2/2007 |
| WO | WO 2007/014760 | 2/2007 |
| WO | WO 2007/014761 | 2/2007 |
| WO | WO 2007/042447 | 4/2007 |
| WO | WO 2007/071730 | 6/2007 |

OTHER PUBLICATIONS

Hydrilla Management in Florida. [online]. University of Florida Department of Fisheries and Aquatic Sciences, Jun. 2005 [retrieved on Nov. 15, 2010] Retrieved from the Internet<URL:http://myfwc.com/docs/WildlifeHabitats/InvasivePlants_HydMgtChIngs06.pdf>, pp. 1-22.*
Gallagher et al., "Reviews of Weed Science," vol. 5, (1990), pp. 115-193.
International Preliminary Report on Patentability (Chapter I), issued in PCT/EP2006/069861, dated Jun. 24, 2008.
Anderson, Lars W.J., "A review of aquatic weed biology and management research conducted by the United States Department of Agriculture—Agricultural Research Service", Pest Manag Sci, 2003, p. 801-813, vol. 59.
Anderson, Lars, W.J., "Movement of 14-C Arsenal® (imazapyr) into monoecious *Hydrilla verticillata* tubers", Res Prog. Rep Weed Sci, 1986 Meeting, p. 30.
Arias, Renee S., et al., "Molecular evolution of herbicides resistance to phytoene desaturase inhibitors in *Hydrilla verticillata* and its potential use to generate herbicide-resistant crops" Pest Manag Sci, 2005, p. 258-268, vol. 61, Search Report.
Kay, S.H. "Response of two alligatorweed biotypes to quinclorac", Journal of Aquatic Plant Management, 1992, p. 35-40, vol. 40
**Document incomplete, Search Report Abstract provided.
Klingman, et al., "Aquatic-Weed Control", Weed Science, Weed Science Society of America, Champaign, IL US 1992, p. 383-402, Search Report.
Netherland, M.D., "Aquatic Plant Management: Invasive species and Chemical Control", Outlooks on Pest Management—Jun. 2005, p. 100-104.
Rattray, M.R., et al., "The Mechanism of Action of Bensulfuron-Methyl on Hydrilla", J. Aquatic Plant Manage., 1993, p. 39-42, vol. 31, Search Report.
International Search Report completed on Dec. 18, 2006 in corresponding International Application PCT/EP2006/069861, filed Dec. 18, 2006.

(Continued)

*Primary Examiner* — Johann Richter
*Assistant Examiner* — Andriae M Holt
(74) *Attorney, Agent, or Firm* — Brinks Hofer Gilson & Lione

(57) ABSTRACT

A method of controlling the aquatic weed Hydrilla verticillata which comprises allowing a herbicidally effective amount of (RS)-2-(4-isopropyl-4-methyl-5-oxo-2-imidazolin-2-yl)-5-methoxymethylnicotinic acid (imazamox) or an agriculturally acceptable salt thereof to act on the aquatic weed and/or its aqueous habitat containing seeds or other propagating organs of said aquatic weed.

16 Claims, No Drawings

OTHER PUBLICATIONS

Capers, Robert S. et al. "Invasive Aquatic Plants", Connecticut Agricultural Experiment Station, Bulletin No. 997, Jan. 2005.

Michel, Albrecht et al. Somatic mutation-mediated evolution of herbicide resistance in the nonindigenous invasive plant *hydrilla* (*Hydrilla verticillata*), Molecular Ecology, 2004, p. 3229-3237, vol. 13.

Nelson, Linda, et al. "Response of Wild Rice to Selected Aquatic Herbicides", U.S. Army Corps of engineers, Sep. 2003.

Tanaka, R.H., et al., "Evaluation of herbicides for control of egeria laboratory, water tank and dam without water flow", Plant Weed, 2002, p. 73-81, vol. 20, Translation provided.

Beck, J., et al., "Quinclorac (BAS 514) and its Herbicide-Combinations in Transplanted Rice in Japan" Proc. 12th Conf. of Asia-Pacific Weed Science Society, 1989, p. 235-244.

Braverman, M.P. et al., "Weed Control in Rice (*Oryza sativa*) with Quinclorac and Bensulfuron Coating of Granular Herbicides and Fertilizer" Weed Technology, 1995, p. 494-498, vol. 9.

Database CA [Online] Chemical Abstracts Service, Columbus, Ohio, US; XP002464636 retrieved from STN-International Database accession No. 141:84041, 2003.

Grossman, Klaus, "Quinclorac belongs to a new class of highly selective auxin herbicides", Weed Science, 1998, p. 707-716, vol. 46.

Kay, S. H., et al., "Response of Two Alligatorweed Biotypes to Quinclorac" Journal of Aquatic Plant Management, Society, Washington, DC US, 1992, pp. 35-40, vol. 30, XP008086947 ISSN: 0146-6623.

Langeland, K., et al. "Efficacy of Herbicide Active Ingredients Against Aquatic Weeds". Biology and Control of Algae. Agronomy Department Document SS AGR 44, Florida Cooperative Extension Service, Institute of Food and Agricultural Sciences, University of Florida, Gainesville, FL 32611, Sep. 2006, http://www.edis.ifas.ufl.edu/.

Mabbayad, M.O., et al., "Herbicide seed treatment for weed control in wet-seeded rice", Tropical Pest Management, 1992, p. 9-12, vol. 38, No. 1.

Street, J.E., et al., "Rice (*Oryza sativa*) Weed Control With Soil Applications of Quinclorac", Weed Technology, 1993, p. 600-604, vol. 7.

"The e-Pesticide Manual (Thirteenth Edition) Version 3.0" 2003, British Crop Protection Council, XP002464632 entry 712: "Quinclorac".

"The e-Pesticide Manual (Thirteenth Edition) Version 3.0" 2003, British Crop Protection Council, XP002464633 entry 713: "Quinmerac".

"The e-Pesticide Manual (Thirteenth Edition) Version 3.0" 2003, British Crop Protection Council, XP002464634 entry 211: "2,4-D".

Zoschke, A., et al., "CGA142'464 plus BAS-514, a new timing-flexible herbicide combination for broadspectrum weed control in rice (*Oryza sativa* L.) in South Korea", 12th Asian-Pacific Weed Science Society Conference, 1989, pp. 245-253, No. 1. and XP002464635 retrieved from STN-International Database accession No. 91:73631.

* cited by examiner

METHOD OF CONTROLLING THE AQUATIC WEED HYDRILLA VERTICILLATA

This application is a National Stage application of International Application No. PCT/EP2006/069861filed Dec. 18, 2006,which claims the benefit of U.S. Provisional Application No. 60/752,906,filed Dec. 23, 2005,the entire contents of which is hereby incorporated herein by reference.

The present invention relates to a method of controlling the aquatic weed Hydrilla verticillata.

Aquatic weeds often have detrimental effects on the environment or the economics of waters and wetlands, for example in the United States of America, in particular in wet areas such as parts of Florida.

The kinds of aquatic weeds and herbicidal or biological methods for fighting aquatic weeds are known, for example from L. W. J. Anderson, Pest Manag. Sci. 59, pages 801-813 (online 2003) or M. D. Netherland et al., Outlooks on Pest Management (Pesticide Outrlook), pages 100-104 or J. Gallagher and W. T. Haller, 1990, Rev. Weed Sci., 5, pages 115-192.

In general terms U.S. Pat. No. 5,334,576 (col. 18) discloses that certain imidazolinone herbicides are useful as aquatic herbicides. Also in general terms U.S. Pat. No. 4,798,619 discloses that certain imidazolinone herbicides are useful as aquatic herbicides (col. 55) and does exemplify (Example 101) the treatment of Eichhornia crassipes (water hyacinth) with e.g. imazapyr or its Calcium salt.

One of the most noxious aquatic weeds is Hydrilla verticillata. Hydrilla verticillata is a submersed, very prolific, mat forming species, which can dominate the aquatic system, e.g. ponds, lakes, creeks, rivers, that it is present in. High densities of Hydrilla verticillata interfere with various water uses.

In a preliminary research report it was stated that imazapyr may be effective in reducing maturation of tubers or preventing successful development of new plants from them (L. W. J. Anderson, Res. Prog. Rep. West. Soc. Weed Sci. 1986 Meet., page 304).

One of the major herbicides used for the control of Hydrilla verticillata has been fluridone. There are now new biotypes of Hydrilla verticillata with an increased tolerance or even resistance to fluridone.

Thus the need for a herbicidal compound for fighting Hydrilla verticillata, in particular for fighting Hydrilla verticillata which is tolerant or resistant to fluridone herbicide is warranted.

Surprisingly, it has now been found that imazamox or agriculturally acceptable salts thereof, optionally in combination with at least one other herbicide B effectively provides growth suppression or control of Hydrilla verticillata.

Imazamox (including its optical isomers) is a known herbicide which is described for example in U.S. Pat. No. 5,334,576. The R-Isomer of imazamox is known from e.g. U.S. Pat. Nos. 5,973,154 or 6,339,158 B1.

The present invention therefore relates to a method of controlling the aquatic weed Hydrilla verticillata which comprises allowing a herbicidally effective amount of (RS)-2-(4-isopropyl-4-methyl-5-oxo-2-imidazolin-2-yl)-5-methoxymethylnicotinic acid (imazamox) or an agriculturally acceptable salt thereof to act on the aquatic weed and/or its aqueous habitat containing seeds or other propagating organs (i.e. tubers, turions) of said aquatic weed.

Habitat means the living space of the plants, e.g. ponds, lakes, rivers, creeks, swamps, canals, reservoirs, and ditches.

A particularly preferred embodiment of the invention comprises the use of imazamox for fighting Hydrilla verticillata wherein the aquatic weed Hydrilla verticillata is resistant to the herbicide fluoridone.

Another particularly preferred embodiment of the invention comprises the use of one of the optical isomers (the R-enantiomer or S-enantiomer) of imazamox, very preferably the R-enantiomer of imazamox.

Another particularly preferred embodiment of the invention comprises method of controlling the aquatic weed Hydrilla verticillata which comprises allowing a herbicidally effective amount of imazamox or an agriculturally acceptable salt thereof to act on the aquatic weed and/or its aqueous habitat containing seeds or other propagating organs of said aquatic weed in the presence of rice plants.

Imazamox can be used in combination with one or more other herbicide(s) or an agriculturally acceptable salt or derivative thereof. Examples of such other herbicide(s) are the herbicides B selected from the following classes b1) to b15):
b1) lipid biosynthesis inhibitors;
b2) acetolactate synthase inhibitors (ALS inhibitors);
b3) photosynthesis inhibitors;
b4) protoporphyrinogen-IX oxidase inhibitors;
b5) bleacher herbicides;
b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitose inhibitors;
b10) inhibitors of the synthesis of long chain fatty acids (VLCFA inhibitors);
b11) cellulose biosynthesis inhibitors;
b12) decoupler herbicides;
b13) auxin herbicides;
b14) auxin transport inhibitors;
b15) other herbicides selected from the group consisting of benzoylprop, flamprop, flamprop-M, bromobutide, chlorflurenol, cinmethylin, methyldymuron, etobenzanid, fosamine, metam, pyributicarb, oxaziclomefone, dazomet, triaziflam and methyl bromide;
all including the agriculturally acceptable salts and the agriculturally acceptable derivatives thereof, provided they have a carboxyl group.

Preferred herbicides of groups b1) to b15) are the compounds listed below:
b1) from the group of the lipid biosynthesis inhibitors:
  chlorazifop, clodinafop, clofop, cyhalofop, diclofop, fenoxaprop, fenoxaprop-p, fenthiaprop, fluazifop, fluazifop-P, haloxyfop, haloxyfop-P, isoxapyrifop, metamifop, propaquizafop, quizalofop, quizalofop-P, trifop, alloxydim, butroxydim, clethodim, cloproxydim, cycloxydim, profoxydim, sethoxydim, tepraloxydim, tralkoxydim, butylate, cycloate, diallate, dimepiperate, EPTC, esprocarb, ethiolate, isopolinate, methiobencarb, molinate, orbencarb, pebulate, prosulfocarb, sulfallate, thiobencarb, tiocarbazil, triallate, vernolate, benfuresate, ethofumesate, bensulide and pinoxaden;
b2) from the group of the ALS inhibitors:
  amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid, pyrithiobac, flucetosulfuron, orthosulfamuron, pyrimisulfan;

b3) from the group of the photosynthesis inhibitors:
atraton, atrazine, ametryne, aziprotryne, cyanazine, cyanatryn, chlorazine, cyprazine, desmetryne, dimethametryne, dipropetryn, eglinazine, ipazine, mesoprazine, methometon, methoprotryne, procyazine, proglinazine, prometon, prometryne, propazine, sebuthylazine, secbumeton, simazine, simeton, simetryne, terbumeton, terbuthylazine, terbutryne, trietazine, ametridione, amibuzin, hexazinone, isomethiozin, metamitron, metribuzin, bromacil, isocil, lenacil, terbacil, brompyrazon, chloridazon, dimidazon, desmedipham, phenisopham, phenmedipham, phenmedipham-ethyl, benzthiazuron, buthiuron, ethidimuron, isouron, methabenzthiazuron, monoisouron, tebuthiuron, thiazafluoron, anisuron, buturon, chlorbromuron, chloreturon, chlorotoluron, chloroxuron, difenoxuron, dimefuron, diuron, fenuron, fluometuron, fluothiuron, isoproturon, linuron, methiuron, metobenzuron, metobromuron, metoxuron, monolinuron, monuron, neburon, parafluoron, phenobenzuron, siduron, tetrafluoron, thidiazuron, cyperquat, diethamquat, difenzoquat, diquat, morfamquat, paraquat, bromobonil, bromoxynil, chloroxynil, iodobonil, ioxynil, amicarbazone, bromofenoxim, flumezin, methazole, bentazone, propanil, pentanochlor, pyridate, and pyridafol;

b4) from the group of the protoporphyrinogen-IX oxidase inhibitors: acifluorfen, bifenox, chlomethoxyfen, chlornitrofen, ethoxyfen, fluorodifen, fluoroglycofen, fluoronitrofen, fomesafen, furyloxyfen, halosafen, lactofen, nitrofen, nitrofluorfen, oxyfluorfen, fluazolate, pyraflufen, cinidonethyl, flumiclorac, flumioxazin, flumipropyn, fluthiacet, thidiazimin, oxadiazon, oxadiargyl, azafenidin, carfentrazone, sulfentrazone, pentoxazone, benzfendizone, butafenacil, pyraclonil, profluazol, flufenpyr, flupropacil, nipyraclofen, etnipromid, and bencarbazone;

b5) from the group of the bleacher herbicides: metflurazon, norflurazon, flufenican, diflufenican, picolinafen, beflubutamid, fluridone, fluorochloridone, flurtamone, mesotrione, sulcotrione, isoxachlortole, isoxaflutole, benzofenap, pyrazolynate, pyrazoxyfen, benzobicyclon, amitrole, clomazone, aclonifen, 4-(3-trifluoromethyl-phenoxy)-2-(4-trifluoromethylphenyl)pyrimidine, known from EP 723960, topramezone, 4-hydroxy-3-{[2-methyl-6-(trifluoromethyl)-3-pyridinyl]carbonyl}bicyclo[3.2.1]oct-3-en-2-one, known from WO 00/15615, 4-hydroxy-3-{[2-(2-methoxyethoxy)methyl-6-(trifluoro-methyl)-3-pyridinyl]carbonyl}bicylo[3.2.1]oct-3-en-2-one, known from WO 01/94339, 4-hydroxy-3-[4-(methylsulfonyl)-2-nitrobenzoyl]bicyclo[3.2.1]-oct-3-en-2-one, known from EP 338992, 2-[2-chloro-4-(methylsulfonyl)-3-[(2,2,2-trifluoroethoxy)methyl]benzoyl]-3-hydroxy-2-cyclohexen-1-one (known from DE 19846792), and pyrasulfotole;

b6) from the group of the EPSP synthase inhibitors: glyphosate;

b7) from the group of the glutamine synthase inhibitors: glufosinate and bilanaphos;

b8) from the group of the DHP synthase inhibitors: asulam;

b9) from the group of the mitose inhibitors:
benfluralin, butralin, dinitramine, ethalfluralin, fluchloralin, isopropalin, methalpropalin, nitralin, oryzalin, pendimethalin, prodiamine, profluralin, trifluralin, arhiprofos-methyl, butamifos, dithiopyr, thiazopyr, propyzamide, tebutam, chlorthal, carbetamide, chlorbufam, chlorpropham and propham;

b10) from the group of the VLCFA inhibitors: acetochlor, alachlor, butachlor, butenachlor, delachlor, diethatyl, dimethachlor, dimethenamid, dimethenamid-P, metazachlor, metolachlor, S-metolachlor, pretilachlor, propachlor, propisochlor, prynachlor, terbuchlor, thenylchlor, xylachlor, allidochlor, CDEA, epronaz, diphenamid, napropamide, naproanilide, pethoxamid, flufenacet, mefenacet, fentrazamide, anilofos, piperophos, cafenstrole, indanofan and tridiphane;

b11) from the group of the cellulose biosynthesis inhibitors: dichlobenil, chlorthiamid, isoxaben and flupoxam;

b12) from the group of the decoupler herbicides: dinofenate, dinoprop, dinosam, dinoseb, dinoterb, DNOC, etinofen and medinoterb;

b13) from the group of the auxin herbicides:
clomeprop, 2,4-D, 2,4,5-T, MCPA, MCPA thioethyl, dichlorprop, dichlorprop-P, mecoprop, mecoprop-P, 2,4-DB, MCPB, chloramben, dicamba, 2,3,6-TBA, tricamba, quinclorac, quinmerac, clopyralid, fluoroxypyr, picloram, triclopyr, benazolin and aminopyralid;

b14) from the group of the auxin transport inhibitors: naptalam, diflufenzopyr;

b15) benzoylprop, flamprop, flamprop-M, bromobutide, chlorflurenol, cinmethylin, methyldymron, etobenzanid, fosamine, metam, pyributicarb, oxaziclomefone, dazomet, triaziflam, methyl bromide;

all including the agriculturally acceptable salts and the agriculturally acceptable derivatives of the respective herbicides, provided they have a carboxyl group.

The herbicides B of groups b1) to b15) are known herbicides, see the quoted literature references and, for example, The Compendium of Pesticide Common Names (http://www.hclrss.demon.co.uk/index.html); Farm Chemicals Handbook 2000 Vol. 86, Meister Publishing Company, 2000; B. Hock, C. Fedtke, R. R. Schmidt, Herbizide, Georg Thieme Verlag, Stuttgart 1995; W. H. Ahrens, Herbicide Handbook, $7^{th}$ Edition, Weed Science Society of America, 1994; and K. K. Hatzios, Herbicide Handbook, Supplement to $7^{th}$ Edition, Weed Science Society of America, 1998.

The categorization of the active compounds according to their mode of action is based on current understanding. If an active compound acts by more than one mode of action, this substance was assigned to only one mode of action.

If imazamox, or the herbicides B are capable of forming geometrical isomers, for example E/Z isomers, it is possible to use both the pure isomers and mixtures thereof in the compositions according to the invention.

If the herbicides B have one or more centers of chirality and, as a consequence, are present as enantiomers or diastereomers, it is possible to use both the pure enantiomers and diastereomers and their mixtures in the compositions according to the invention.

Imazamox does and the herbicides B may have functional groups which can be ionized, thus imazamox and the herbicides B can also be used in the form of their agriculturally acceptable salts. In general, the salts of those cations or the acid addition salts of those acids are suitable whose cations and anions, respectively, have no adverse effect on the action of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, furthermore ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)eth-1-ylammonium, di(2-hydroxyeth-1-yl)ammonium, benzyltrimethylammonium, benzyltriethylammonium, furthermore phosphonium ions, sulfonium ions, preferably tri($C_1$-$C_4$-alkyl)sulfonium such as trimethylsulfonium, and sulfoxonium ions, preferably tri($C_1$-$C_4$-alkyl)sulfoxonium.

Anions of useful acid addition salts are primarily chloride, bromide, fluoride, iodide, hydrogen sulfate, methyl sulfate, sulfate, dihydrogen phosphate, hydrogen phosphate, nitrate, dicarbonate, carbonate, hexafluorosilicate, hexafluorophosphate, benzoate and the anions of $C_1$-$C_4$-alkanoic acids, preferably formate, acetate, propionate and butyrate.

According to the invention, the active compounds which carry a carboxyl group can, instead of the active compounds mentioned above, also be employed in the form of an agriculturally acceptable derivative, for example as amides such as mono- or di-$C_1$-$C_6$-alkylamides or arylamides, as esters, for example as allyl esters, propargyl esters, $C_1$-$C_{10}$-alkyl esters or alkoxyalkyl esters, and also as thioesters, for example as $C_1$-$C_{10}$-alkyl thioesters.

Preferred mono- and di-$C_1$-$C_6$-alkylamides are the methyl- and the dimethylamides. Preferred arylamides are, for example, the anilidines and the 2-chloroanilides. Preferred alkyl esters are, for example, the methyl, ethyl, propyl, isopropyl, butyl, isobutyl, pentyl, mexyl (1-methylhexyl) or isooctyl (2-ethylhexyl) esters. Preferred $C_1$-$C_4$-alkoxy-$C_1$-$C_4$-alkyl esters are the straight-chain or branched $C_1$-$C_4$-alkoxyethyl esters, for example the methoxyethyl, ethoxyethyl or butoxyethyl esters. An example of the straight-chain or branched $C_1$-$C_{10}$-alkyl thioesters is the ethyl thioester.

In binary compositions which comprise imazamox and at least one herbicide B, the weight ratio of the active compounds imazamox:B is usually in the range from 1:500 to 10:1, preferably in the range from 1:100 to 10:1, in particular in the range from 1:50 to 10:1 and particularly preferably in the range from 1:25 to 5:1.

Regarding combinations of imazamox and herbicides B, preference is given to those compositions of the invention which comprise imazamox in combination with at least one and preferably exactly one herbicidally active compound selected from the group consisting of b2) ALS inhibitors, preferably imazapyr; b5) bleacher herbicides, preferably fluridone; b 13) auxin herbicides, preferably quinclorac; b14) auxin transport inhibitors, preferably diflufenzopyr; and endothall.

For application ready-to-use preparations in the form of crop protection products can be employed. Imazamox and optionally component B may be present in suspended, emulsified or dissolved form and can be formulated jointly or separately. The application forms depend entirely on the intended use.

The preparations can be applied, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, broadcasting or watering. The use forms depend on the intended use; in any case, they should ensure the finest possible distribution of the active compounds.

Depending on the form in which the ready-to-use preparations are present, they comprise one or more liquid or solid carriers, if appropriate surfactants and if appropriate further auxiliaries which are customary for formulating crop protection products. The person skilled in the art is sufficiently familiar with the recipes for such formulations.

The ready-to-use preparations may comprise auxiliaries, which are customary for formulating crop protection products, which auxiliaries may also comprise a liquid carrier.

Suitable inert additives with carrier function are essentially: mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the active compound (s) as such or dissolved in an oil or solvent, can be homogenized in water by means of wetting agent, tackifier, dispersant or emulsifier. Alternatively, it is possible to prepare concentrates consisting of active substance, wetting agent, tackifier, dispersant or emulsifier and, if desired, solvent or oil, and these concentrates are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, of alkyl- and alkylarylsulfonates, of alkyl sulfates, lauryl ether sulfates and fatty alcohol sulfates, and salts of sulfated hexa, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ether or polyoxypropylene alkyl ether, lauryl alcohol polyglycol ether acetate, sorbitol esters, lignosulfite waste liquors or methylcellulose.

Powders, materials for spreading and dusts can be prepared by mixing or concomitant grinding of the active substances with a solid carrier.

Granules, e.g. coated granules, impregnated granules and homogeneous granules, can be prepared by binding the active ingredient (s) to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin
such as cereal meal, tree bark meal, wood meal and nutshell meal, cellulose powders, or other solid carriers.

The concentrations of the active compound (s) in the ready-to-use preparations can be varied within wide ranges. In general, the formulations comprise from 0.001 to 98% by weight, preferably 0.01 to 95% by weight, of active ingredient (s). The active ingredient (s) are employed in a purity of from 90% to 100%, preferably 95% to 100% (according to NMR spectrum).

The preparations can, for example, be formulated as follows:

I    20 parts by weight of the active compound(s) in question are dissolved in a composition composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient.

II   20 parts by weight of the active compound(s) in question are dissolved in a composition composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient.

III  20 parts by weight of the active compound(s) in question are dissolved in a composition composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient.

IV   20 parts by weight of the active compound(s) in question are mixed thoroughly with 3 parts by weight of sodium diisobutyl-naphthalenesulfonate, 17 parts by weight of the sodium salt of a lignosulfonic acid from a sulfite waste liquor and 60 parts by weight of pulverulent silica gel, and the composition is ground in a hammer mill. Finely distributing the composition in 20 000 parts by weight of water gives a spray composition which comprises 0.1% by weight of the active ingredient.

V    3 parts by weight of the active compound(s) in question are mixed with 97 parts by weight of finely divided kaolin. This gives a dust which comprises 3% by weight of the active ingredient.

VI   20 parts by weight of the active compound(s) in question are mixed intimately with 2 parts by weight of calcium dodecylbenzene-sulfonate,
     8 parts by weight of fatty alcohol polyglycol ether, 2 parts by weight of the sodium salt of a phenol-urea-formaldehyde condensate and 68 parts by weight of a paraffinic mineral oil. This gives a stable oily dispersion.

VII  1 part by weight of the active compound(s) in question is dissolved in a composition composed of 70 parts by weight of cyclohexanone, 20 parts by weight of ethoxylated isooctylphenol and 10 parts by weight of ethoxylated castor oil. This gives a stable emulsion concentrate.

VIII 1 part by weight of the active compound(s) in question is dissolved in a composition composed of 80 parts by weight of cyclohexanone and 20 parts by weight of Wettol EM 31 (nonionic emulsifier based on ethoxylated castor oil). This gives a stable emulsion concentrate.

The components imazamox and/or B can be formulated jointly or separately.

The components imazamox and as the case may be B can be applied jointly or separately, simultaneously or successively, before, during or after emergence of the plants.

The required application rate of the pure active compound(s) imazamox, optionally in combination with B without formulation auxiliary, depends on the density of the undesired vegetation, on the development stage of the plants, on the climatic conditions of the location where the composition is used and on the application method. In general, the application rate is from 1 to 1000 ppb (parts per billion), preferably from 10 to 500 ppb and in particular from 25 to 300 ppb of active substance.

The preparations are applied to the water body as either a surface or subsurface application. Application can be carried out by customary spraying techniques using, for example, water as carrier and spray liquid rates of from about 50 to 1 000 l/ha (for example from 300 to 400 l/ha). Application of the preparations by the low-volume and the ultra-low-volume method is possible, as is their application in the form of microgranules.

When applying imazamox by the method according to this invention Hydrilla verticillata is fought slowly, meaning the biomass of Hydrilla verticillata in aqueous systems, for example ponds, lakes, creeks, rivers or swamps is declining slowly and gradually. This is a big advantage compared to other herbicides for control of Hydrilla verticillata—for example the herbicide endothall—which is also used in fighting Hydrilla verticillata and which exhibits very rapid, contact control of Hydrilla verticillata. Rapid, contact biomass reduction under high infestation levels is undesirable in that it for example can lead to rapid oxygen depletion in the aqueous system, which then may lead for example to significant fish mortality.

The following examples illustrate the invention without limiting it.

The effect of the use of imazamox or mixtures thereof with herbicides such as B) according to the present invention on the growth of Hydrilla verticillata was demonstrated by greenhouse container tests.

Materials and Methods:

To begin the experiment, PVC cylinders were filled and maintained with a volume of 4000 ml of dechlorinated water that was maintained at room temperature (24° C.). To each cylinder, an established Hydrilla verticillata plant (potted in sand mixture) was transferred into the water column. Hydrilla plants were selected for uniformity and length of shoot growth (approx 15 cm). Plants were allowed to equilibrate in the columns for 24 hrs prior to herbicide treatment. Experimental treatments included an untreated control, and imazamox at 50 and 100 ppb of actual acid equivalent of herbicide. Treatments were applied to water columns by the use of a pipette. Amount of herbicide applied was based on the total volume of the cylinders (4000 ml). After initial herbicide treatment, the water columns were gently stirred to ensure uniform distribution. Treatments were arranged as a completely random design with 3 replications. Each cylinder was considered the experimental unit. Greenhouse conditions were maintained at 24/18° C. (day/night) cycle for the duration of the experiment. Natural day length was supplemented with halogen lighting to provide a 14 h photoperiod. Water level in the cylinders was periodically checked and maintained at the 4000 ml level for the duration of the study. After 11 weeks of exposure, Hydrilla shoot lengths were measured to ascertain herbicide effects. The results are given in the following table.

TABLE 1

Response of *Hydrilla verticillata* to static exposure of imazamox herbicide at 11 WAT.

| Treatment | Rate (ppb) | *Hydrilla* Shoot Length (cm) |
|---|---|---|
| Control | — | 30.4 |
| Imazamox | 50 | 18.5 |
| Imazamox | 100 | 12.3 |
| Imazamox + quinclorac | 100 + 250 | 9.6 |

Results showed that after the exposure period imazamox had a significant effect on the growth of hydrila. In addition to the growth suppression, visual symptomology included reduction in plant vigour, chlorosis and reduction of internodal length.

Intensity of symptoms tended to be rate responsive. The mixture of imazamox plus quinclorac also showed significant effects.

We claim:

1. A method of controlling the aquatic weed Hydrilla verticillata which comprises contacting said aquatic weed and/or its aqueous habitat containing seeds or other propagating organs with a herbicidally effective amount of (RS)-2-(4-isopropyl-4-methyl-5-oxo-2-imidazolin-2-yl)-5-methoxymethylnicotinic acid or an agriculturally acceptable salt thereof.

2. The method as claimed in claim 1, wherein the aquatic weed Hydrilla verticillata is resistant to the herbicide fluoridone.

3. The method as claimed in claim 1, conducted in the presence of rice plants.

4. A method of controlling the aquatic weed Hydrilla verticillata which comprises contacting said aquatic weed and/or its aqueous habitat containing seeds or other propagating organs with a herbicidally effective amount of the R-enatiomer or the S-enatiomer of 2-(4-isopropyl-4-methyl-5-oxo-2-imidazolin-2-yl)-5-methoxymethylnicotinic acid.

5. The method as claimed in claim 1, wherein (RS)-2-(4-isopropyl-4-methyl-5-oxo-2-imidazolin-2-yl)-5-methoxymethylnicotinic acid is used in combination with one or more other herbicide(s).

6. The method as claimed in claim 1, wherein (RS)-2-(4-isopropyl-4-methyl-5-oxo-2-imidazolin-2-yl)-5-methoxymethylnicotinic acid is used in combination with one or more other herbicide(s) B selected from the following classes b1) to b15):
- b1) lipid biosynthesis inhibitors;
- b2) acetolactate synthase inhibitors (ALS inhibitors);
- b3) photosynthesis inhibitors;
- b4) protoporphyrinogen-IX oxidase inhibitors;
- b5) bleacher herbicides;
- b6) enolpyruvyl shikimate 3-phosphate synthase inhibitors (EPSP inhibitors);
- b7) glutamine synthetase inhibitors;
- b8) 7,8-dihydropteroate synthase inhibitors (DHP inhibitors);
- b9) mitose inhibitors;
- b10) inhibitors of the synthesis of long chain fatty acids (VLCFA inhibitors);
- b11) cellulose biosynthesis inhibitors;
- b12) decoupler herbicides;
- b13) auxin herbicides;
- b14) auxin transport inhibitors;
- b15) other herbicides selected from the group consisting of benzoylprop, flamprop, flamprop-M, bromobutide, chlorflurenol, cinmethylin, methyldymuron, etobenzanid, fosamine, metam, pyributicarb, oxaziclomefone, dazomet, triaziflam and methyl bromide;

all including the agriculturally acceptable salts and the agriculturally acceptable derivatives thereof, provided they have a carboxyl group.

7. A method of controlling the aquatic weed Hydrilla verticillata resistant to the herbicide fluoridone which comprises contacting said aquatic weed and/or its aqueous habitat containing seeds or other propagating organs with a herbicidally effective amount of (RS)-2-(4-isopropyl-4-methyl-5-oxo-2-imidazolin-2-yl)-5-methoxymethylnicotinic acid or an agriculturally acceptable salt thereof.

8. The method as claimed in claim 7, conducted in the presence of rice plants.

9. A method of controlling the aquatic weed Hydrilla verticillata resistant to the herbicide fluoridone which comprises contacting said aquatic weed and/or its aqueous habitat containing seeds or other propagating organs with a herbicidally effective amount of the R-enatiomer or the S-enatiomer of 2-(4-isopropyl-4-methyl-5-oxo-2-imidazolin-2-yl)-5-methoxymethylnicotinic acid.

10. The method as claimed in claim 7, wherein (RS)-2-(4-isopropyl-4-methyl-5-oxo-2-imidazolin-2-yl)-5-methoxymethylnicotinic acid is used in combination with one or more other herbicide(s).

11. The method as claimed in claim 7, wherein (RS)-2-(4-isopropyl-4-methyl-5-oxo-2-imidazolin-2-yl)-5-methoxymethylnicotinic acid is used in combination with one or more other herbicide(s) B selected from the following classes b1) to b15):
- b1) lipid biosynthesis inhibitors;
- b2) acetolactate synthase inhibitors (ALS inhibitors);
- b3) photosynthesis inhibitors;
- b4) protoporphyrinogen-IX oxidase inhibitors;
- b5) bleacher herbicides;
- b6) enolpyruvyl shikimate 3-phosphate synthase inhibitors (EPSP inhibitors);
- b7) glutamine synthetase inhibitors;
- b8) 7,8-dihydropteroate synthase inhibitors (DHP inhibitors);
- b9) mitose inhibitors;
- b10) inhibitors of the synthesis of long chain fatty acids (VLCFA inhibitors);
- b11) cellulose biosynthesis inhibitors;
- b12) decoupler herbicides;
- b13) auxin herbicides;
- b14) auxin transport inhibitors;
- b15) other herbicides selected from the group consisting of benzoylprop, flamprop, flamprop-M, bromobutide, chlorflurenol, cinmethylin, methyldymuron, etobenzanid, fosamine, metam, pyributicarb, oxaziclomefone, dazomet, triaziflam and methyl bromide;

all including the agriculturally acceptable salts and the agriculturally acceptable derivatives thereof, provided they have a carboxyl group.

12. The method of claim 1, wherein said aquatic weed and/or its aqueous habitat containing seeds or other propagating organs is contacted with from 25 to 300 ppb of (RS)-2-(4-isopropyl-4-methyl-5-oxo-2-imidazolin-2-yl)-5-methoxymethylnicotinic acid or an agriculturally acceptable salt thereof.

13. The method of claim 4, wherein said aquatic weed and/or its aqueous habitat containing seeds or other propagating organs is contacted with from 25 to 300 ppb of (RS)-2-(4-isopropyl-4-methyl-5-oxo-2-imidazolin-2-yl)-5-methoxymethylnicotinic acid or an agriculturally acceptable salt thereof.

14. The method of claim 7, wherein said aquatic weed and/or its aqueous habitat containing seeds or other propagating organs is contacted with from 25 to 300 ppb of (RS)-2-(4-isopropyl-4-methyl-5-oxo-2-imidazolin-2-yl)-5-methoxymethylnicotinic acid or an agriculturally acceptable salt thereof.

15. The method of claim 9, wherein said aquatic weed and/or its aqueous habitat containing seeds or other propagating organs is contacted with from 25 to 300 ppb of (RS)-2-(4-isopropyl-4-methyl-5-oxo-2-imidazolin-2-yl)-5-methoxymethylnicotinic acid or an agriculturally acceptable salt thereof.

16. The method of claim 1, wherein (RS)-2-(4-isopropyl-4-methyl-5-oxo-2-imidazolin-2-yl)-5-methoxymethylnicotinic acid is used in combination with endothall.

* * * * *